(12) United States Patent
Randall et al.

(10) Patent No.: US 6,514,261 B1
(45) Date of Patent: Feb. 4, 2003

(54) DELIVERY MECHANISM FOR IMPLANTABLE STENT

(75) Inventors: Scott L. Randall, Mesa, AZ (US); Brendan J. McCrea, Ballwin, MO (US); Christopher J. Brooks, Glen Head, NY (US); Donald Van Royen, New York, NY (US)

(73) Assignee: Impra, Inc., Tempe, AZ (US)

( * ) Notice: Subject to any disclaimer, the term of this patent is extended or adjusted under 35 U.S.C. 154(b) by 0 days.

(21) Appl. No.: 09/409,210

(22) Filed: Sep. 30, 1999

Related U.S. Application Data
(60) Provisional application No. 60/102,498, filed on Sep. 30, 1998.

(51) Int. Cl.[7] .................................................. A61B 17/00
(52) U.S. Cl. ........................................ 606/108; 604/528
(58) Field of Search ........................ 623/1.11, 1.12, 623/1.23; 606/108; 604/528

(56) References Cited

U.S. PATENT DOCUMENTS

| | | |
|---|---|---|
| 844,478 A | 2/1907 | Spalding |
| 4,411,653 A | 10/1983 | Razi ............................ 604/157 |
| 4,616,648 A | 10/1986 | Simpson |
| 4,651,738 A | 3/1987 | Demer et al. |
| 4,679,557 A | 7/1987 | Opie et al. |
| 4,921,484 A | 5/1990 | Hillstead ..................... 604/104 |
| 5,002,560 A | 3/1991 | Machold et al. .............. 606/198 |
| 5,007,898 A | 4/1991 | Rosenbluth et al. ........... 604/54 |
| 5,021,046 A | 6/1991 | Wallace .......................... 604/97 |
| 5,024,668 A | 6/1991 | Peters et al. ................. 606/194 |
| 5,047,015 A | 9/1991 | Foote et al. .................... 606/99 |
| 5,084,060 A | 1/1992 | Freund et al. ................ 606/192 |
| 5,152,776 A | 10/1992 | Pinchuk ........................ 606/192 |
| 5,160,341 A | * 11/1992 | Brenneman et al. ......... 606/198 |
| 5,201,750 A | 4/1993 | Höcherl et al. ............... 606/180 |
| 5,201,753 A | 4/1993 | Lampropoulos et al. ..... 606/192 |
| 5,201,757 A | 4/1993 | Heyn et al. ................... 606/198 |
| 5,273,026 A | 12/1993 | Wilk ............................ 606/198 |
| 5,282,472 A | 2/1994 | Companion et al. ......... 606/108 |
| 5,325,848 A | 7/1994 | Adams et al. ................ 606/108 |
| 5,336,234 A | 8/1994 | Vigil et al. ................... 606/159 |
| 5,346,498 A | 9/1994 | Greelis et al. ................ 606/108 |
| 5,389,100 A | 2/1995 | Bacich et al. ................ 606/108 |
| 5,391,172 A | 2/1995 | Williams et al. ............. 606/108 |
| 5,409,478 A | 4/1995 | Gerry et al. ...................... 606/1 |
| 5,415,664 A | 5/1995 | Pinchuk ........................ 606/108 |
| 5,443,477 A | 8/1995 | Marin et al. .................. 606/198 |
| 5,464,408 A | 11/1995 | Duc ............................. 606/108 |
| 5,507,727 A | 4/1996 | Crainich ........................ 604/97 |
| 5,571,114 A | 11/1996 | Devanaboyina .............. 604/108 |
| 5,591,172 A | 1/1997 | Bachmann et al. .......... 606/108 |
| 5,601,568 A | 2/1997 | Chevillon et al. ........... 606/108 |
| 5,601,591 A | 2/1997 | Edwards et al. ............. 606/198 |

(List continued on next page.)

FOREIGN PATENT DOCUMENTS

| | | |
|---|---|---|
| EP | 0 536 610 A1 | 4/1993 |
| EP | 0 564 783 A1 | 10/1993 |
| EP | 0 705 578 A1 | 4/1996 |

*Primary Examiner*—Cary E. O'Connor
(74) *Attorney, Agent, or Firm*—Morrison & Foerster

(57) ABSTRACT

A delivery mechanism for an implantable stent which provides a high mechanical advantage to the surgeon and convenient operation so as to facilitate smooth withdrawal of an outer catheter sheath following placement of the stent in the desired location within the patient's vessel. Preferred embodiments include a moving rail actuated by a V-shaped lever, a hydraulic actuator, a rack and pinion drive, and a power screw system. The delivery mechanism has a movable member that is attached to the outer catheter sheath so that actuating the mechanism results in an incremental movement of the moveable member, which in turn results in an incremental movement of the outer catheter sheath. Once the outer catheter sheath is retracted from the stent, the stent is deployed into the patient's vessel and the remaining parts of the mechanism, including an inner tube, an atraumatic tip, and a stabilizing element, are easily removed.

31 Claims, 10 Drawing Sheets

U.S. PATENT DOCUMENTS

| | | | |
|---|---|---|---|
| 5,603,698 A | 2/1997 | Roberts et al. | 604/104 |
| 5,618,300 A | 4/1997 | Marin et al. | 606/198 |
| 5,665,103 A | 9/1997 | Lafontaine et al. | 606/192 |
| 5,690,645 A | 11/1997 | Van Erp | 606/108 |
| 5,695,517 A | 12/1997 | Marin et al. | 606/198 |
| 5,697,948 A | 12/1997 | Marin et al. | 606/198 |
| 5,702,418 A | 12/1997 | Ravenscroft | 606/198 |
| 5,707,376 A | 1/1998 | Kavteladze et al. | 606/108 |
| 5,720,742 A | 2/1998 | Zacharias | 606/1 |
| 5,741,270 A | 4/1998 | Hansen et al. | 606/108 |
| 5,749,918 A | 5/1998 | Hogendijk et al. | 606/194 |
| 5,755,686 A | 5/1998 | O'Neill et al. | 604/53 |
| 5,759,186 A | 6/1998 | Bachmann et al. | 606/108 |
| 5,766,184 A | 6/1998 | Matsuno et al. | 606/142 |
| 5,779,688 A | 7/1998 | Imran et al. | 604/283 |
| 5,779,702 A | 7/1998 | Fard | 606/53 |
| 5,868,755 A | 2/1999 | Kanner et al. | 606/108 |
| 5,944,727 A * | 8/1999 | Ahari et al. | 606/108 |
| 5,968,052 A | 10/1999 | Sullivan, III et al. | 606/108 |
| 6,056,759 A * | 5/2000 | Fiedler | 606/108 |
| 6,113,608 A | 9/2000 | Monroe et al. | 606/108 |
| 6,146,415 A * | 11/2000 | Fitz | 623/1.11 |
| 6,238,402 B1 | 5/2001 | Sullivan, III et al. | 606/108 |
| 6,251,132 B1 * | 6/2001 | Ravenscroft et al. | 623/1.11 |
| 6,350,278 B1 * | 2/2002 | Lenker et al. | 623/1.12 |

* cited by examiner

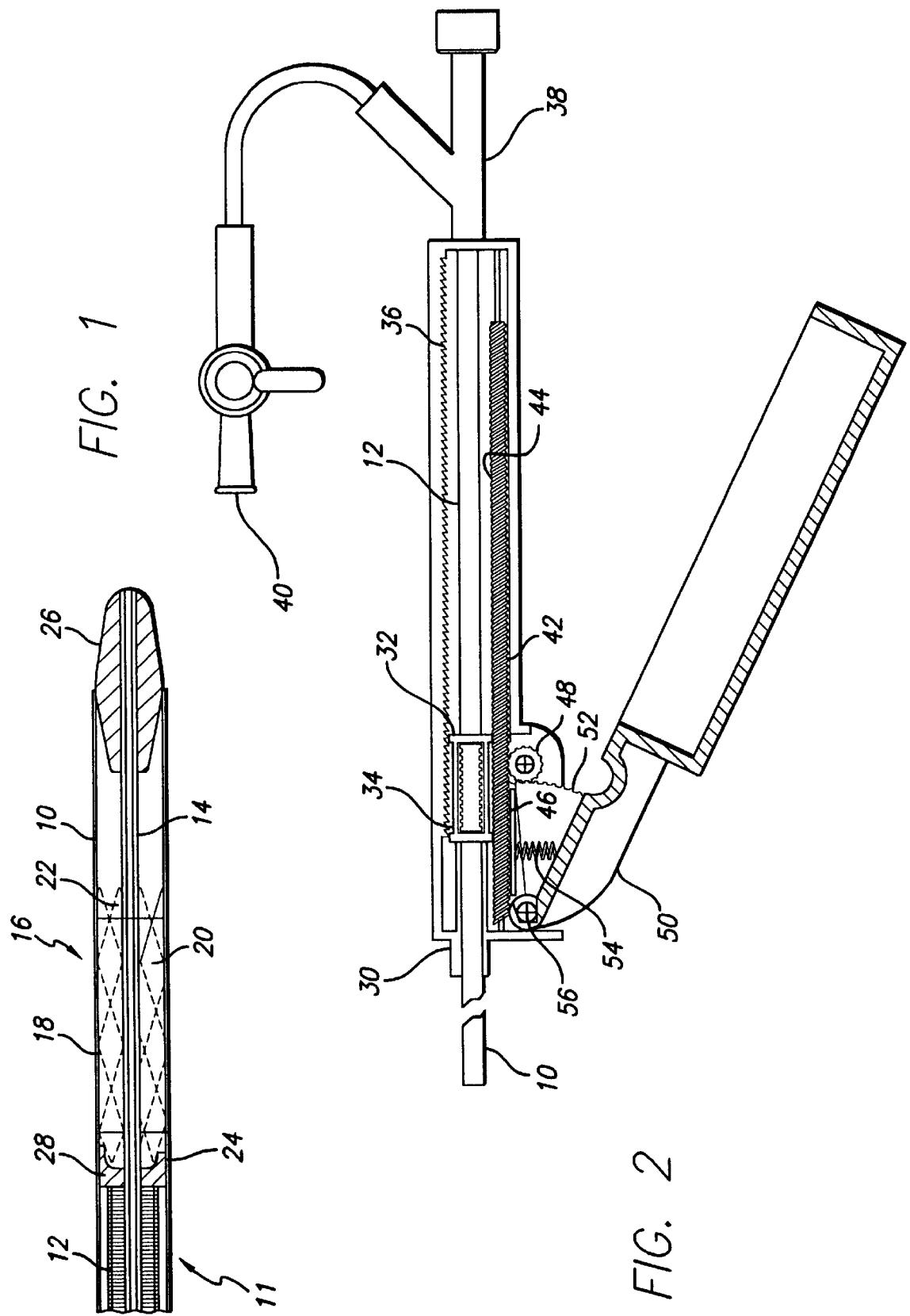

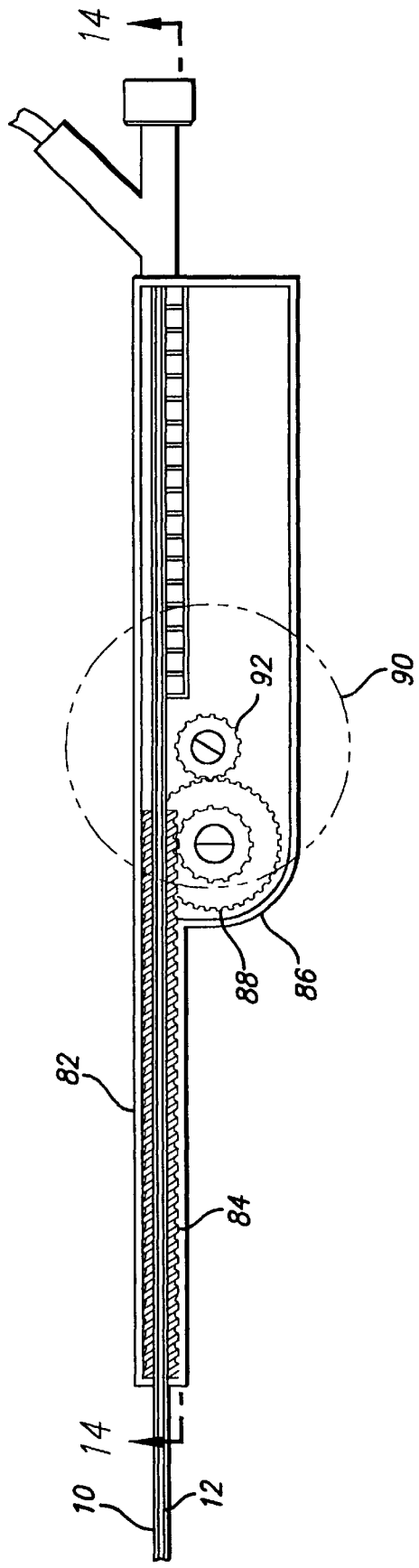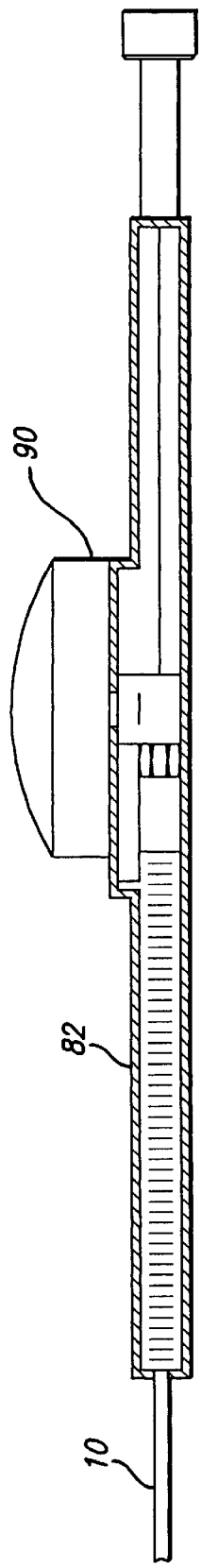

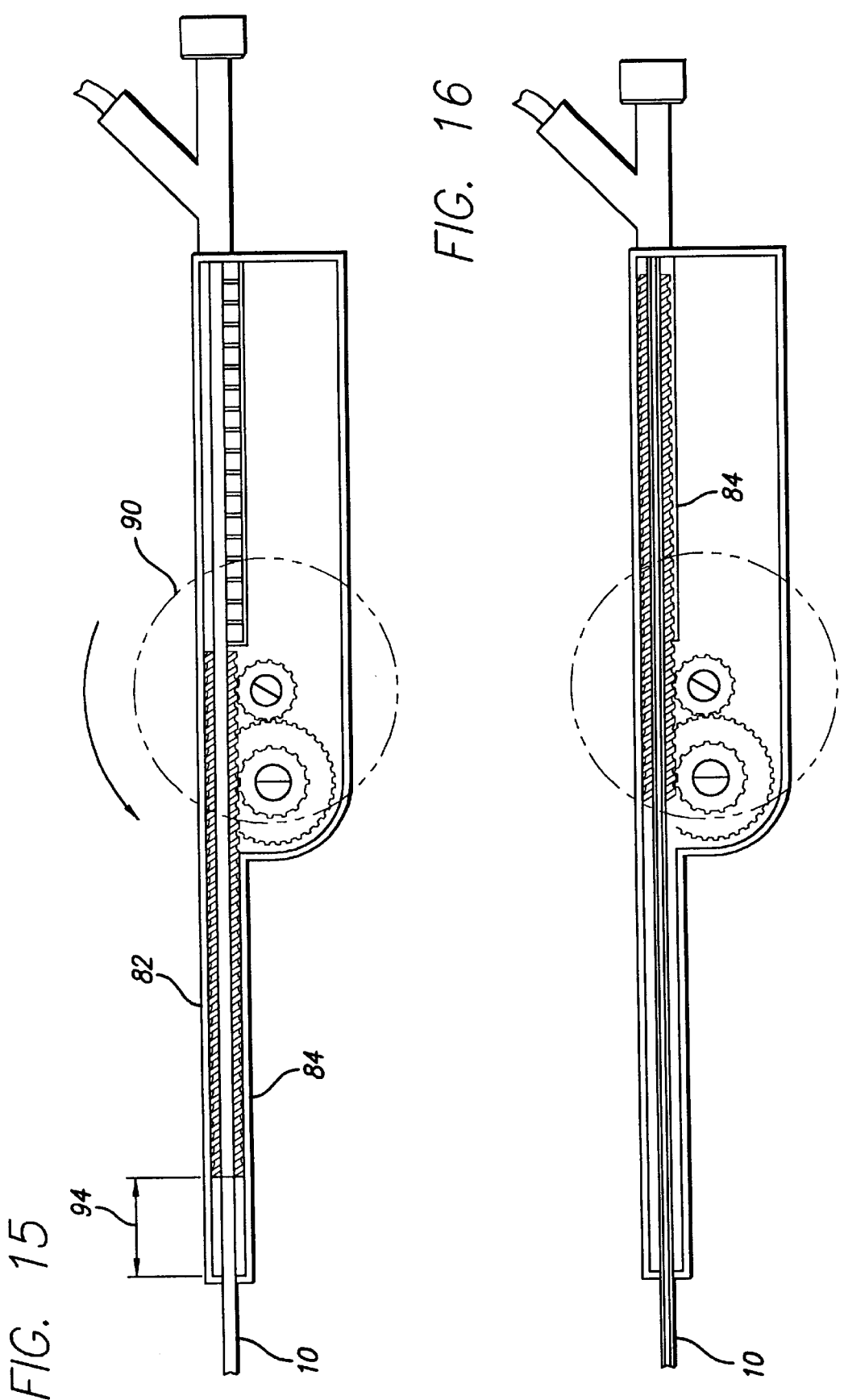

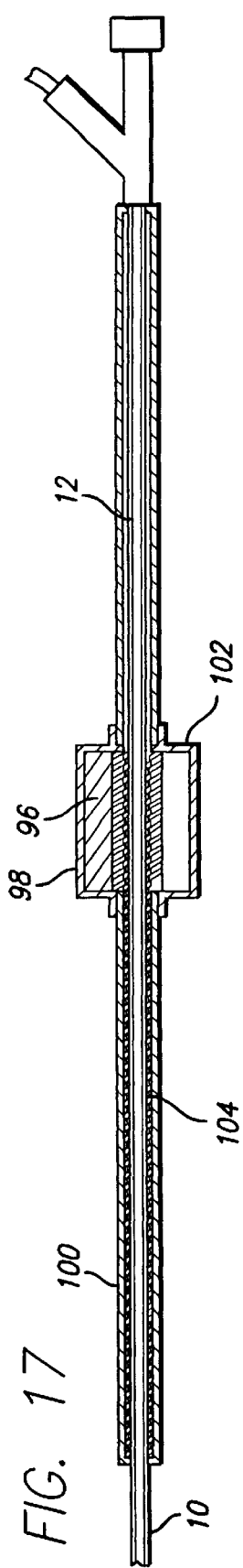
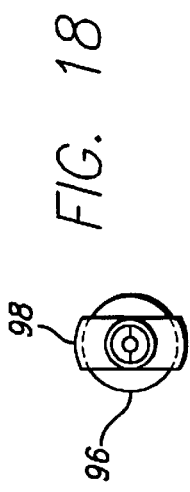
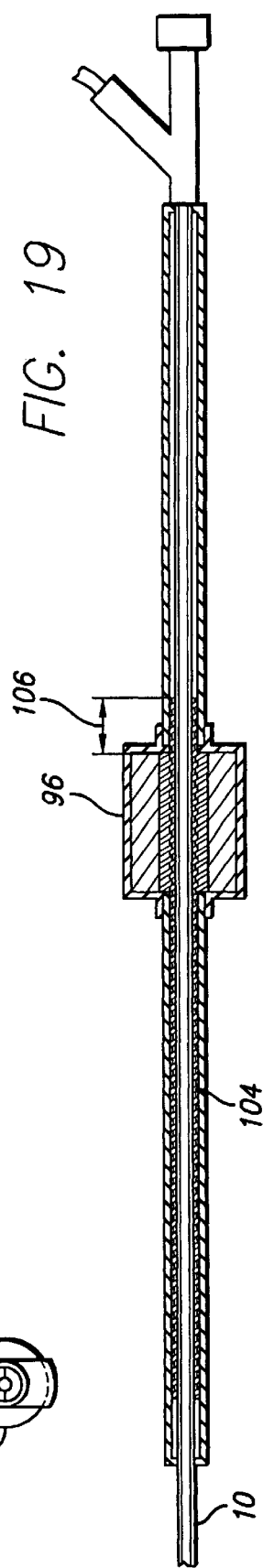
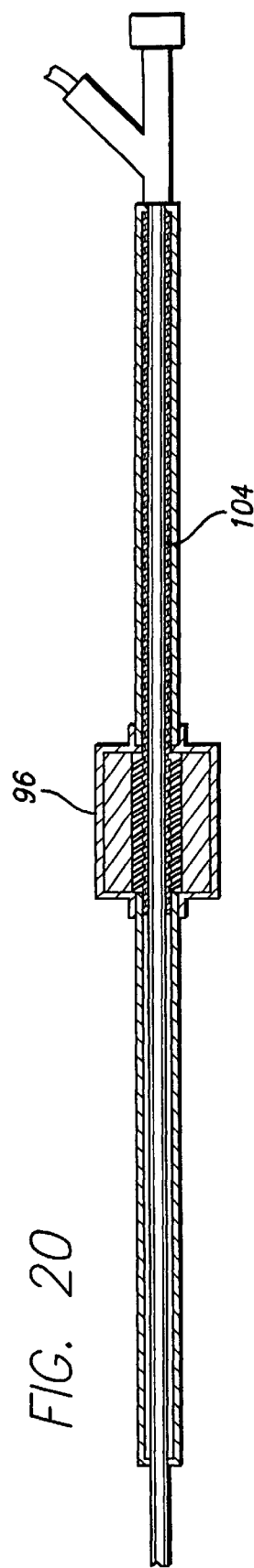
FIG. 17
FIG. 18
FIG. 19
FIG. 20

DELIVERY MECHANISM FOR IMPLANTABLE STENT

CROSS-REFERENCE TO RELATED APPLICATIONS

This application claims the benefit of U.S. Provisional Application No. 60/102,498, filed Sep. 30, 1998.

BACKGROUND OF THE INVENTION

1. Field of the Invention

The present invention relates to implantable medical devices. More particularly, the present invention relates to mechanisms for implanting a self-expanding stent graft which is used to sustain a weakened body vessel.

2. Description of Related Art

Various diseases of blood vessels or hollow organs cause a stenosis or complete occlusion of their lumen, which results in a decrease or complete loss of their functional attributes. Various implantable prosthetic devices for sustaining a blood vessel or hollow organ lumen typically have a tubular-shaped frame body which is introduced into the vessel or hollow organ and fixed in the necessary location to sustain the lumen.

A commonly used implant is a tubular-shaped wire frame known as a stent graft. In one type of stent graft, the wire frame is made of self-expanding nickel-titanium (nitinol) shape memory alloy which is laser cut and encapsulated within two layers of expanded polytetrafluoroethylene (ePTFE). The layers of ePTFE are processed such that the material forms a monolithic structure, fully enclosing the metallic stent where the cover is present. The encapsulation is intended to prevent restenosis of the vessel. The inner blood contacting lumen of the stent graft is impregnated with carbon. Typically, one or both ends of the stent graft is flared and free of encapsulation in order to facilitate anchoring within the vessel. The nitinol alloy is placed into the body during surgery at room temperature. As it increases to body temperature, it expands to its desired size. Balloon angioplasty may be done after implantation of the stent to set its final shape.

In order to introduce the stent into the body vessel, it is placed within a tubular sheath catheter. When the device is positioned at the desired location, it is released from the tubular sheath and permitted to expand radially against the wall of the vessel. When the outer sheath is removed, the physician must be careful to avoid migration of the stent away from the desired location. Typical prior art devices employ a simple ratchet mechanism in conjunction with the outer sheath and an inner lumen. The inner lumen is maintained stationary to fix the stent in position and the outer lumen is drawn away from the stent by means of the ratchet mechanism actuated by a spring loaded trigger. Each pull on the trigger causes the outer sheath to retract by an amount corresponding to the stroke of the trigger. An anchor to which the outer sheath is attached includes a tooth which engages with each tooth of the ratchet mechanism. This mechanism has drawbacks in that it is awkward to operate and difficult to maintain steady so that the stent graft does not migrate away from its desired position during sheath retraction.

SUMMARY OF THE INVENTION

The present invention is directed to a stent delivery mechanism which is both easy to operate and facilitates extremely precise stent positioning. Several different configurations are described. In the first embodiment, a simple V-shaped grip aligned generally longitudinally with the catheter to be deployed is utilized. A mechanical advantage gear mechanism is employed, which operates in conjunction with a ratchet to smoothly retract a sheath hub to which the outer sheath of the catheter is attached. The mechanism is easy to grasp and actuate in any rotational configuration. The V-shaped mechanism includes a body which contains the ratchet and a drive gear lever handle. The lever handle interacts with a drive pinion to drive the ratchet by a predetermined amount, thus retracting the sheath hub by a corresponding amount. The drive gear lever handle mechanism provides both the mechanical advantage, which results in movement of the outer sheath by a relatively small amount for a large displacement of the lever handle, and a much smoother operation than the direct ratchet operation of the prior art device.

A second embodiment of the invention employs a hydraulic mechanism to both provide the mechanical advantage and achieve extremely smooth retraction operation. In addition, the use of hydraulics, as opposed to other systems, creates positive positioning so that the actuator will not cause any unexpected motion. The hydraulic system may be actuated by means of a drive plunger similar to the operation of a syringe, or may be equipped with a lever handle to allow a gripping action to be employed for actuation.

In a third embodiment, a rack and pinion drive system operated by a thumb wheel is employed. The rack and pinion drive system also provides a desirable mechanical advantage and promotes smooth operation.

In a fourth embodiment, a power screw drive system is employed. This drive system is actuated by a thumb driven concentric drive knob which rotates to retract an internal power screw to which the outer sheath is secured. Again, a mechanical advantage is provided to promote smooth retraction of the outer sheath.

In order to further facilitate the stent deployment, the inner lumen of the delivery system may be formed of a metal spring, which is contained in its fully compressed state. The use of such a spring for the inner lumen provides significant advantages in that it is extremely flexible, enabling introduction of the catheter into the body and proper positioning of the stent, and yet is very rigid and non-compressible so as to maintain the stent in the desired position during outer sheath retraction.

BRIEF DESCRIPTION OF THE DRAWINGS

The invention will be described by reference to the accompanying drawings, wherein:

FIG. 1 is a cross-sectional view of the end of a catheter illustrating a stent to be implanted;

FIG. 2 is a cross-sectional view of a first embodiment of the stent delivery mechanism of the present invention incorporating a moving rail mechanism;

FIG. 13 is a cross-sectional view of a third embodiment of the stent delivery mechanism of the present invention employing a rack and pinion thumb actuated drive system;

FIG. 14 is a view of the system of FIG. 13 along line 14—14;

FIGS. 15 and 16 are cross-sectional views illustrating the operation of the drive system of FIG. 13;

FIG. 17 is a cross-sectional view of a fourth embodiment of the stent delivery mechanism of the present invention employing a power screw drive system;

FIG. 18 is an end plan view illustrating the drive knob and collar configuration of the system of FIG. 17; and FIGS. 19 and 20 are cross-sectional views illustrating the operation of the power screw drive system of FIG. 17.

DETAILED DESCRIPTION OF THE PREFERRED EMBODIMENTS

Figure 3:
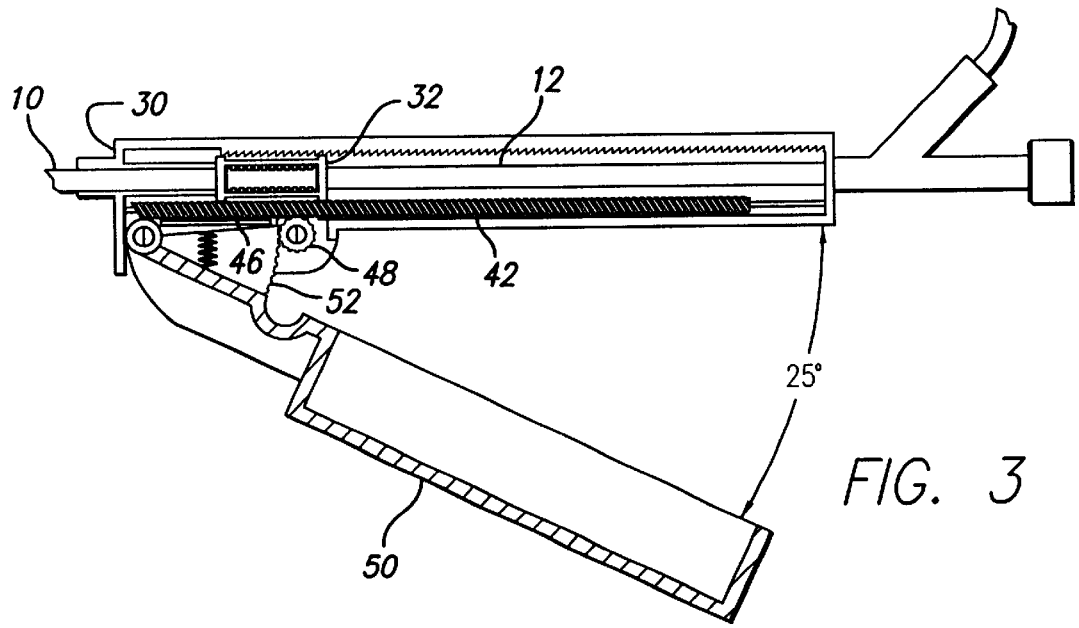
FIGS. 3–6 are cross-sectional views illustrating the retraction operation of the moving rail system.
Figure 4:
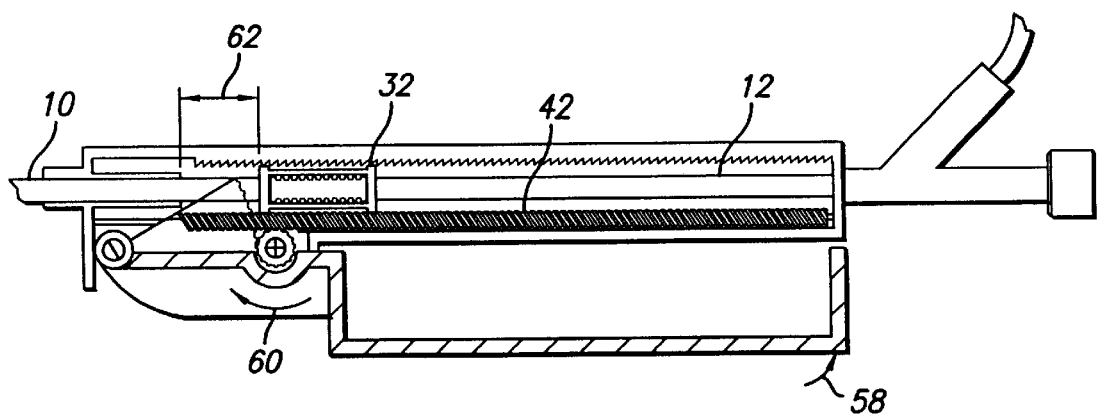

The following description is of the best presently contemplated modes of carrying out the invention. The description is made for illustrating the general principles of the invention and is not to be taken in a limiting sense.

FIG. 1 illustrates the distal end of a catheter 11 having a stent 16 carried within it for implantation into the body of a patient. The proximal end of the catheter 11 is connected to any of the delivery mechanisms to be described, and the catheter 11 is of sufficient length to reach the point of implantation of the stent 16 from the introduction point into the body. The catheter 11 includes an outer sheath 10, a middle tube 12 which in the preferred embodiment is formed of a compressed spring, and a flexible (e.g., polyamide) inner tube 14. The outer sheath 10 preferably has an ePTFE liner with a polyether blocked amide plastic (pebax) basecoat with reinforced braid, and an external layer of pebax. A stent 16 for implantation into a patient is carried within the outer sheath 10. The stent 16 includes a nitinol memory metal alloy frame 18 which is formed in a criss-cross pattern which may be laser cut. Most or all of the length of the stent is encapsulated within two layers of ePTFE to form a monolithic body structure 20, fully enclosing the metallic stent 16 both internally and externally where the cover 20 is present. One or both ends of the stent 16 may be left uncovered as illustrated at 22 and 24 to provide anchoring within the vessel where the stent 16 is to be implanted.

A radiopaque atraumatic tip 26 is secured to the end of the inner tube 14 of the catheter. The atraumatic tip 26 has a rounded end and is gradually sloped to aid in the movement of the catheter through the body vessel. The atraumatic tip 26 is radiopaque so that its location may be monitored by appropriate equipment during the surgical procedure. The inner tube 14 is hollow so as to accommodate a guide wire, which is commonly placed in the vessel prior to insertion of the catheter, although the invention may employ a solid inner section and be used without a guide wire. Inner tube 14 has sufficient kink resistance to engage the vascular anatomy without binding during placement and withdrawal of the delivery system. In addition, inner tube 14 is of sufficient size and strength to allow saline injections without rupture.

A generally cup-shaped element 28 is provided within the catheter 11 adjacent the rear end of the stent 16 and is attached to the end of the spring 12 by appropriate means, e.g., the cup element 28 may be plastic wherein the spring 12 is molded into its base, or the cup element 28 may be stainless steel wherein the spring 12 is secured by welding or the like. The open end of the cup element 28 serves to compress the end 24 of the stent 16 in order to provide a secure interface between the stent 16 and the spring 12. Alternatively, instead of a cup shape, the element 28 could be formed of a simple disk having either a flat or slightly concave surface for contacting the end 24 of the stent 16.

In order to deploy the stent 16 inside a body vessel during a surgical procedure, the catheter 11 is introduced into the designated vessel via an introducer positioned at the skin of the patient. As mentioned above, a guide wire may have previously been introduced into the vessel, in which case the catheter 11 is introduced by passing the tip 26 over the end of the guide wire outside of the patient and moving the catheter 11 along the path within the vessel which has been established by the guide wire.

The position of the catheter 11 is tracked by monitoring the tip 26 by means of a fluoroscope. When the catheter 11 is at the desired location i.e., when the stent 16 is positioned at the location where it is be implanted, the movement of the catheter 11 is halted. The catheter 11 must then be removed, leaving the stent 16 in place at the desired location within the vessel. This is accomplished by initially retracting the outer sheath 10, i.e., towards the left in FIG. 1, until it no longer covers the stent 16. The spring 12 is maintained in a fixed position and, in conjunction with the cup element 28, serves to maintain the stent 16 in its desired position during the retraction of the outer sheath 10. After the outer sheath 10 has been retracted such that it no longer covers the stent 16 and the stent 16 is expanded, the tip 26 can be pulled back through the stent 16 until the tip 26 abuts the outer sheath 10. As illustrated, the diameter of the tip 26 is slightly greater than the inner diameter of stent 16 when it is inside the outer sheath 10. The stent 16 will expand as it heats up to body temperature as a result of its memory metal characteristics. The tip 26 is then pulled through the center of the stent 16 after the stent 16 has expanded following withdrawal of the sheath 10. Once the tip 26 has been pulled back against the outer sheath 10, the catheter 11 can be removed from the vessel of the patient. This retraction procedure ensures that the tip 26 does not get caught on or embedded in any body vessel when being pulled out of the patient.

As discussed above, the tube spring 12 is maintained stationary during the withdrawal of the outer sheath 10 and serves to keep the stent 16 in its desired location. The tube spring 12 is very well suited for this task since it has extremely low compression in a longitudinal direction once it is fully compressed. It is also well suited for the introduction of the catheter 11 into the body vessel, since it is extremely flexible. Alternatively, other materials, such as various plastics materials, could be employed as the middle tube 12, so long as the compression is low to maintain stent positioning and the necessary flexibility is provided for moving through the vessel. In order to properly deploy the stent 16, the outer sheath 10 must be smoothly retracted while the tube spring 12 maintains its position. The present invention provides a number of mechanisms intended to perform this operation with maximum ease of use and minimal stent migration.

FIG. 2 illustrates a first embodiment of a delivery mechanism for implanting the stent 16. This mechanism is generally in the form of a V-shaped lever device having a housing shell 30 from which the outer sheath 10 extends. The sheath 10 is secured to a pawl/sheath hub 32. A spring pawl 34 attached to the hub 32 engages a ratchet 36 which is integrated into the housing shell 30. Movement of the sheath hub 32 within the housing shell 30 is thus constrained to moving to the right as shown in FIG. 2. The tube spring 12 is secured in a fixed position to a guide wire port 38. The interior of the device may be flushed by means of a flush stop cock 40. A ratchet rail 42 is provided at the bottom of the housing shell 30 and is reciprocal back and forth within the shell 30. The rail 42 includes ratchet teeth 44 on the upper side which engage with the spring pawl 34 and a rack gear 46 on the bottom surface thereof which engages a pinion 48. The pinion 48 is rotated by means of a lever handle 50 which includes a drive gear 52. The lever handle 50 is spring biased by means of a spring 54 to its open position. Other types of springs, such as a spring contained within the pivot point 56 of the lever handle could alternatively be employed.

Figure 5:
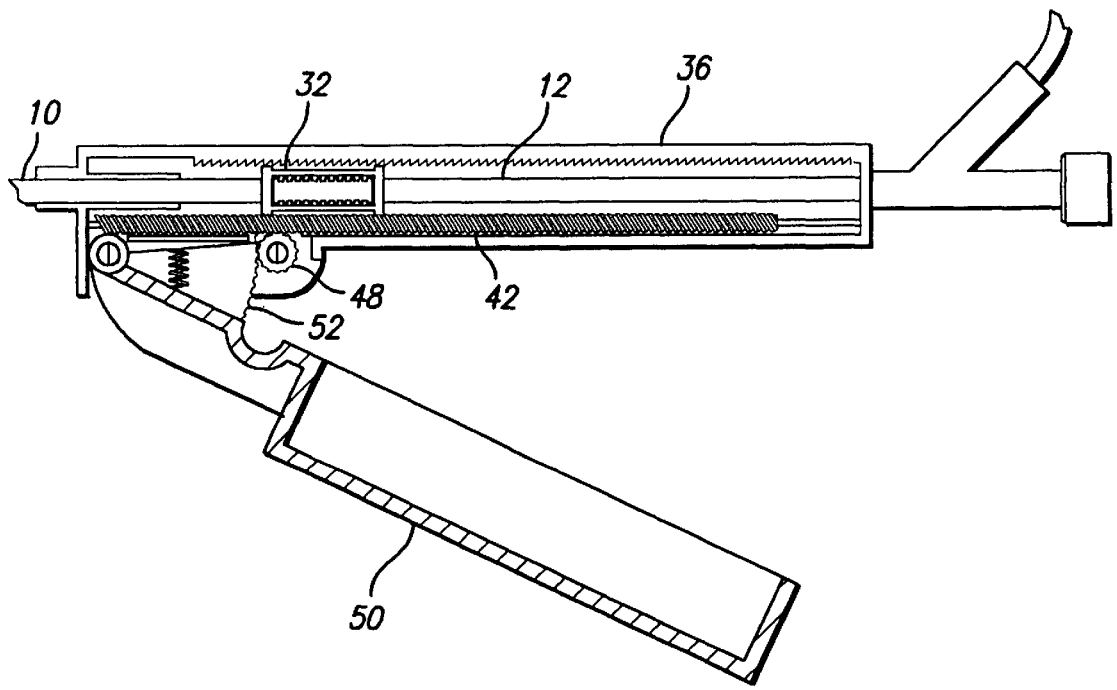

The operation of the device of FIG. 2 will be described with reference to FIGS. 3–6. Initially, as illustrated in FIG. 3, the handle 50 is in its open position, which forms an angle of approximately twenty-five degrees with the housing shell 30. When the handle is squeezed, bringing it adjacent to the housing shell as indicated by arrow 58 in FIG. 4, the drive gear 52 rotates the pinion 48 in a clockwise direction as illustrated by arrow 60. The pinion 48 drives the rail 42 to the right, which in turn drives the sheath hub 32 to the right, thus extracting the outer sheath 10 by an incremental distance illustrated at 62. In the described device, the incremental distance is approximately 1 cm. Referring to FIG. 5, when the handle 50 is released, the spring action returns it to the open position, thus rotating the pinion 48 counter-clockwise and returning the rail 42 to its leftward position. The sheath hub 32 is maintained stationary by the ratchet 36.

Figure 6:
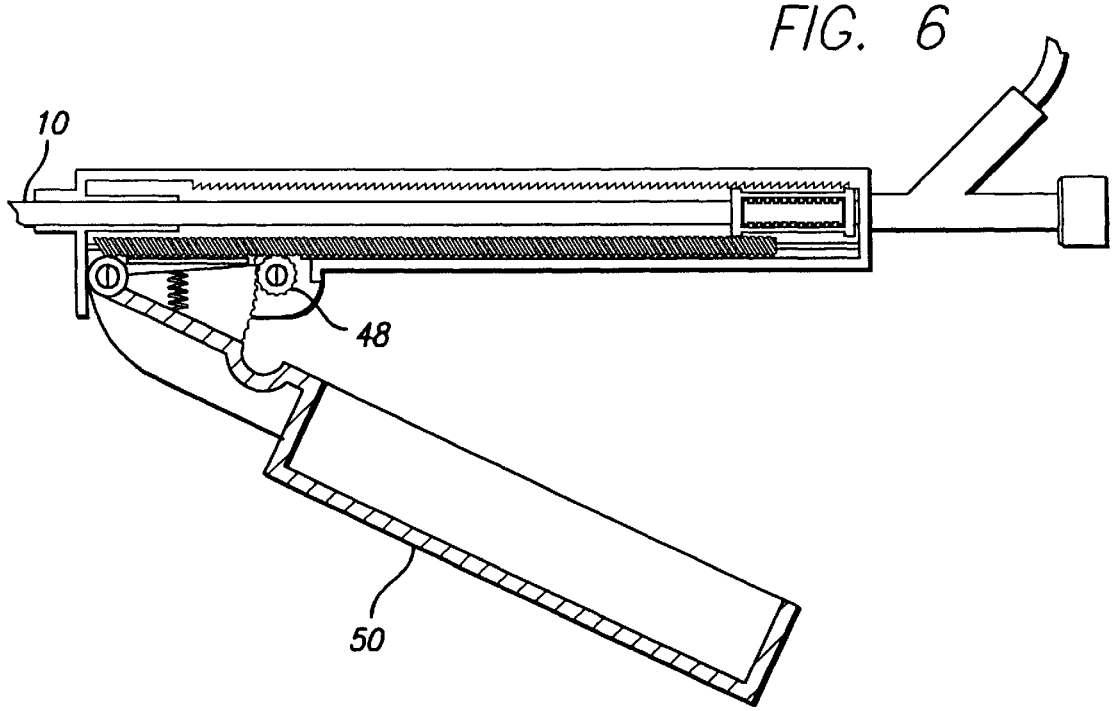

The described device is intended for use with stents of approximately 40–100 mm in length. In order to fully retract the outer sheath 10, the lever handle 50 must be closed and opened a number of times. FIG. 6 illustrates the mechanism in which the handle 50 has been operated to move the hub 32, and therefore the outer sheath 10, back to its completely rightmost position. In this position (or sooner depending upon the length of the stent) the outer sheath 10 will be completely away from the stent 16, allowing the stent 16 to expand. As described above, once the stent 16 expands, the inner tube 14 and tip 26 are pulled back through the middle of the stent 16 until the tip 26 is tight against the outer sheath 10. The entire catheter 11 can then be removed, leaving the stent 16 in place at the desired location.

Figure 7:
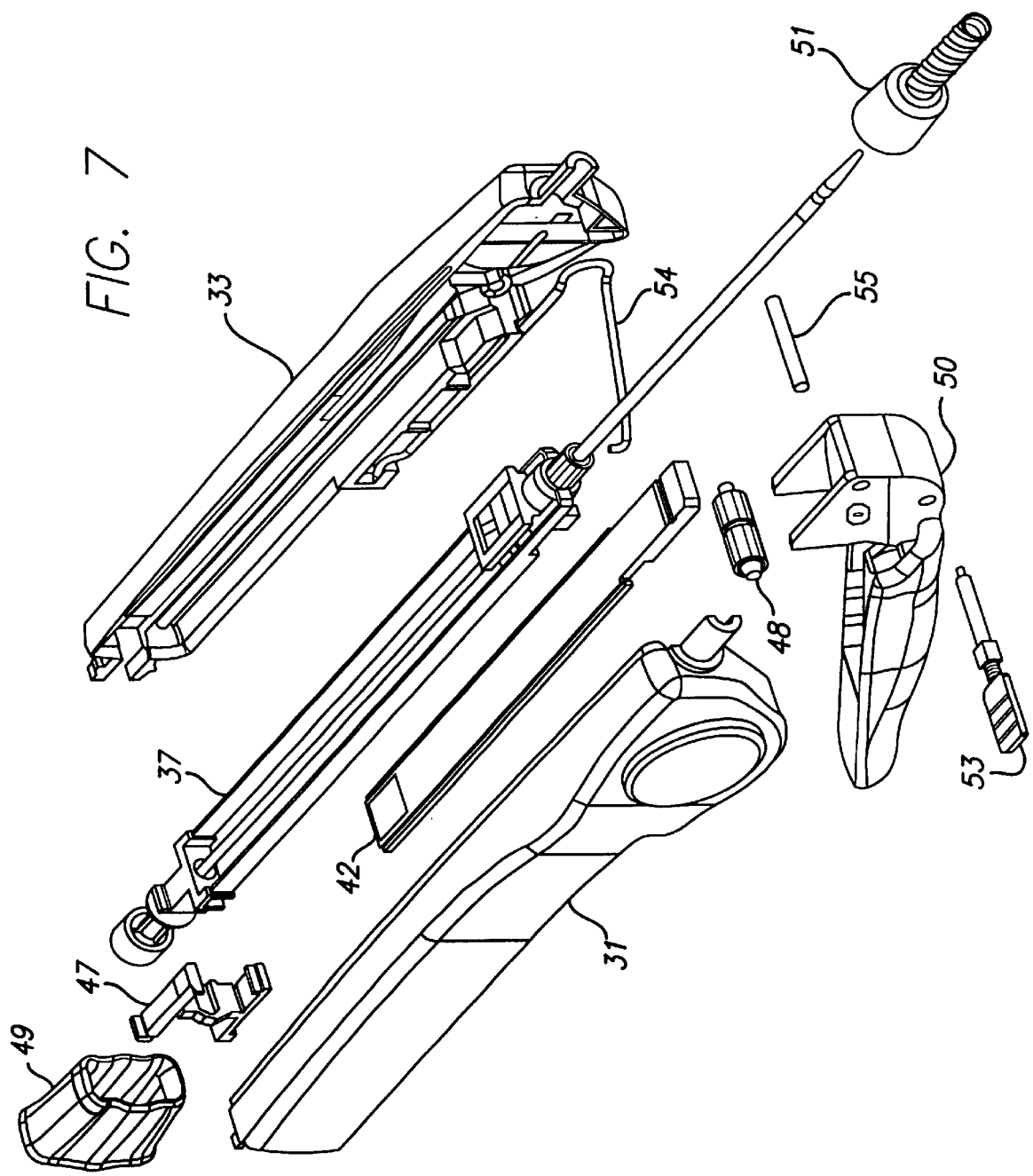
FIG. 7 is an exploded view of a preferred embodiment of the stent delivery mechanism shown in FIG. 2.

A preferred embodiment of the device shown in FIG. 2 is illustrated by the exploded view in FIG. 7. In this view, a left housing assembly 31 and a right housing assembly 33 can be seen. An inner catheter assembly 37 is disposed between the housing assemblies 31 and 33 to support the tube spring 12 as well as the spring pawl 34. A strain relief member 51 fits over the end of housing shell 30 to reduce any potential pressure caused in the actuation of the mechanism. A safety pin 53 is insertable into the lever handle 50 for additional protection. Upon completion of the deployment of the stent 16 and the retraction of outer sheath 10, a retractor sleeve 49 is pulled back slightly, releasing a retractor latch 47 from its locked position on the inner catheter assembly 37. The inner catheter assembly 37, which is coupled to the inner tube 14, is pulled back away from the housing assemblies 31 and 33 in order to retract the inner tube 14 far enough so that tip 26 is snuggly against the outer sheath 10. The catheter 11, including the outer sheath 10, the inner tube 14 and the tip 26 can then be removed from the body. Retraction of the catheter 11 in this manner ensures that the tip 26 can not get caught on anything outside of the body or inside the delivery mechanism.

The gear mechanism including the lever gear 52, pinion 48 and rack 46 is designed to provide a mechanical advantage of approximately 4:1. The mechanical advantage along with the rotating pinion configuration provides very smooth and linear operation with minimal fly back during the return stroke. In addition, the lever handle configuration is extremely convenient, as it can be easily operated in almost any rotational orientation. This is important due to the fact that when a catheter is introduced into the patient, it is often necessary to rotate the catheter in order for it to most easily follow the desired path through the vessel to the stent location. Therefore, the final orientation when the stent is to be deployed is variable. The configuration of the V-shaped lever handle mechanism enables a simple gripping action to be applied, and is easily gripped by the surgeon regardless of its final orientation. Generally, approximately ten cycles (i.e., squeezing and releasing) of the lever handle 50 are necessary to fully remove the outer sheath 10 from the stent. The configuration of this embodiment enables retraction to be done in a very smooth and linear fashion.

Figure 8:
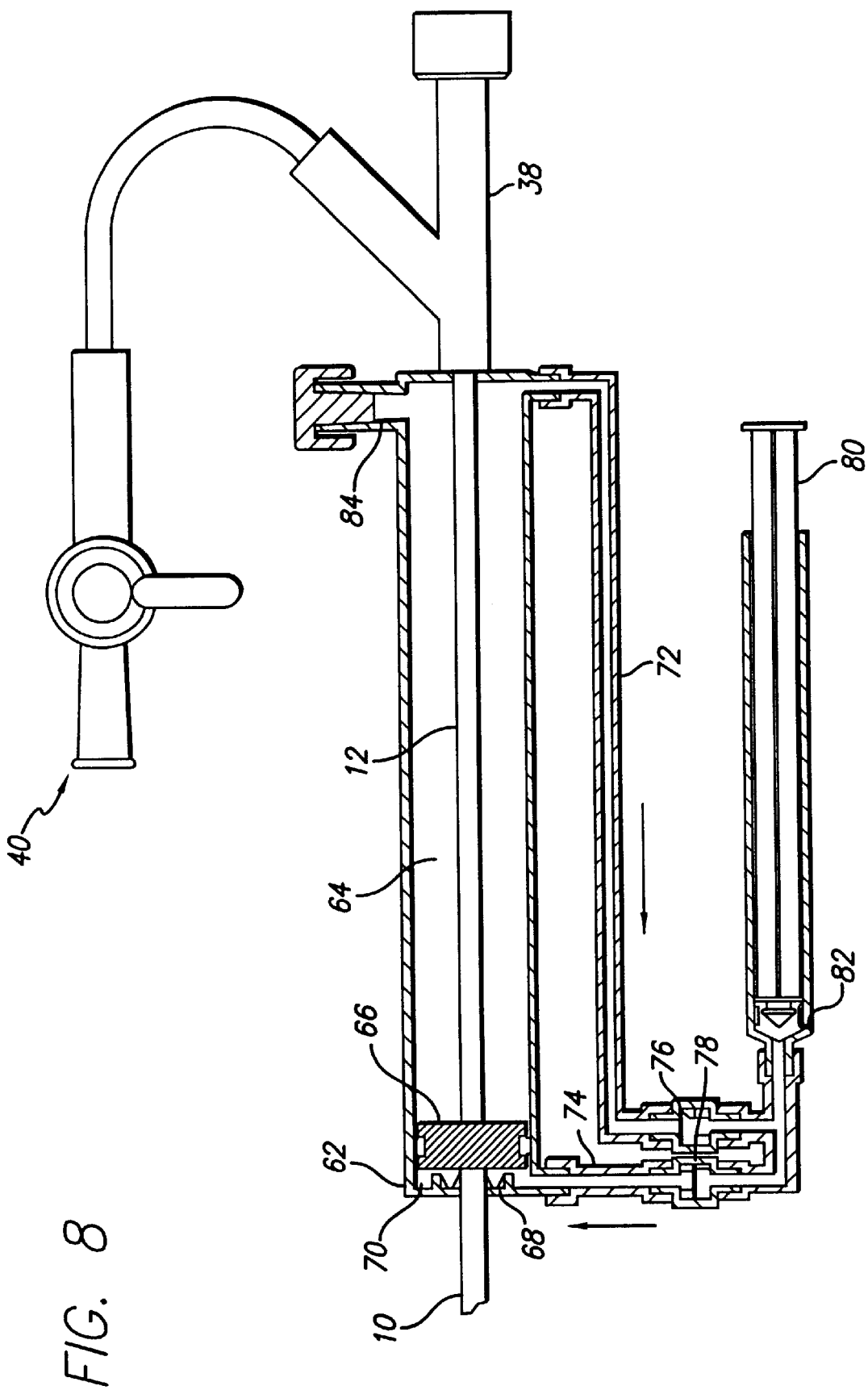
FIG. 8 is a cross-sectional view of a second embodiment of the stent delivery mechanism of the present invention incorporating a hydraulic mechanism

A second embodiment of the stent delivery mechanism is illustrated in FIG. 8. This delivery mechanism employs a hydraulic system to achieve extremely smooth operation. A housing 62 defines a reservoir chamber 64 within which is carried a piston 66. The outer sheath 10 is connected to the piston 66 to be moved therewith. A V-cup seal 68 prevents leakage of the hydraulic fluid carried within the housing. A piston displacement chamber 70 is defined between the piston 66 and the opening through which the sheath 10 exits.

Conduits 72 and 74 are coupled to opposite ends of the piston housing 62. Directional check valves 76 and 78 are contained within the conduits 72 and 74, respectively. A drive plunger 80 is contained within a plunger housing 82. Hydraulic fluid, such as saline solution, is provided through a port 84.

Figure 9:
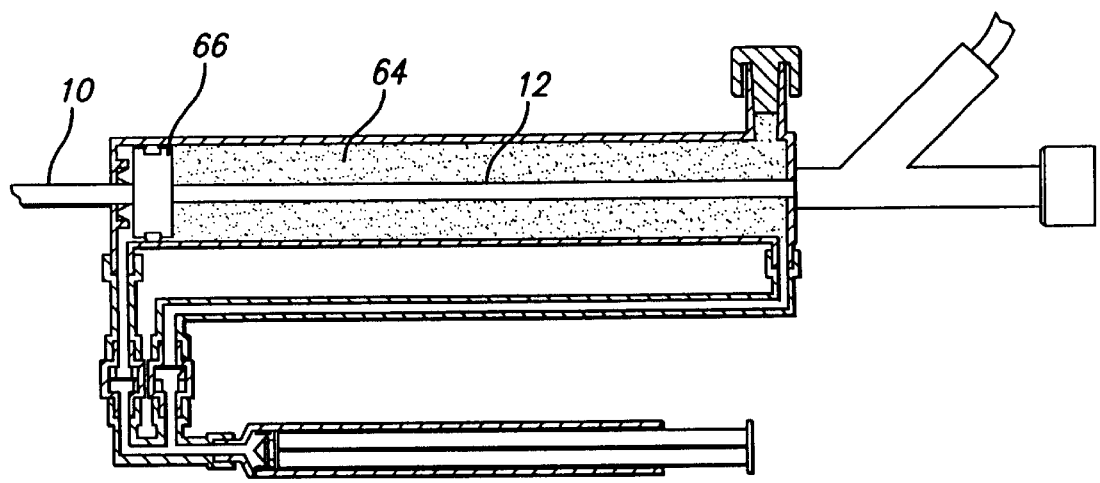
FIGS. 9–12 are cross-sectional views illustrating the operation of the embodiment of FIG. 7.
Figure 10:
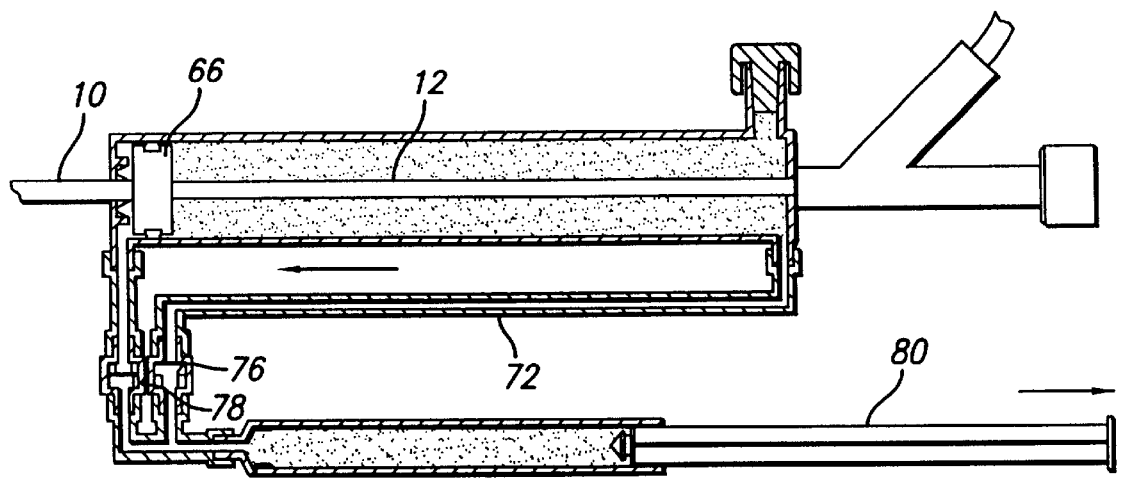

The operation of the hydraulic mechanism will be described with reference to FIGS. 9–12. In FIG. 9, the reservoir 64 is filled with fluid and the system is ready for operation. In FIG. 10, the plunger 80 is pulled rearward and transfers saline from the reservoir 64 through the conduit 72 via valve 76. The valve 76 is open in this state and the valve 78 is closed.

Figure 11:
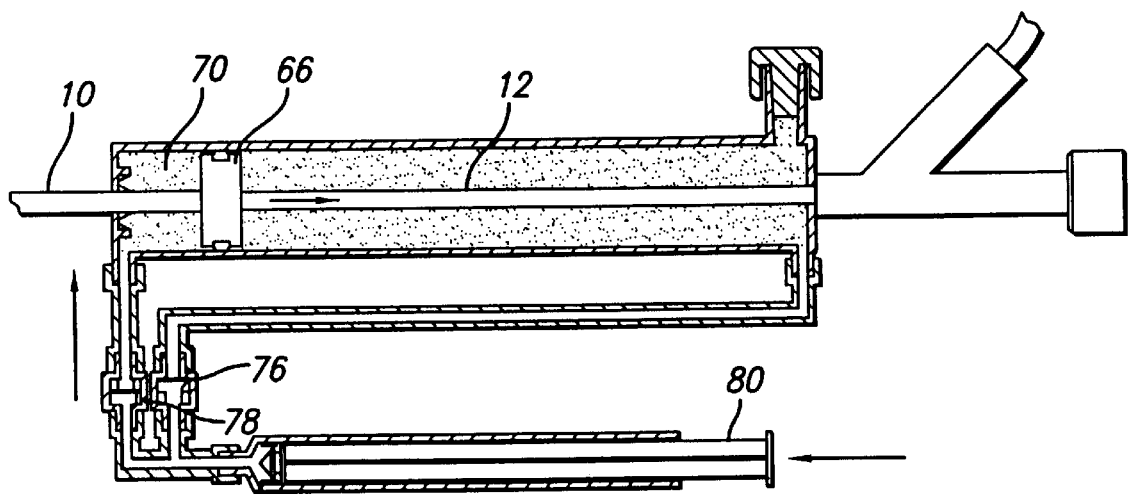
Figure 12:
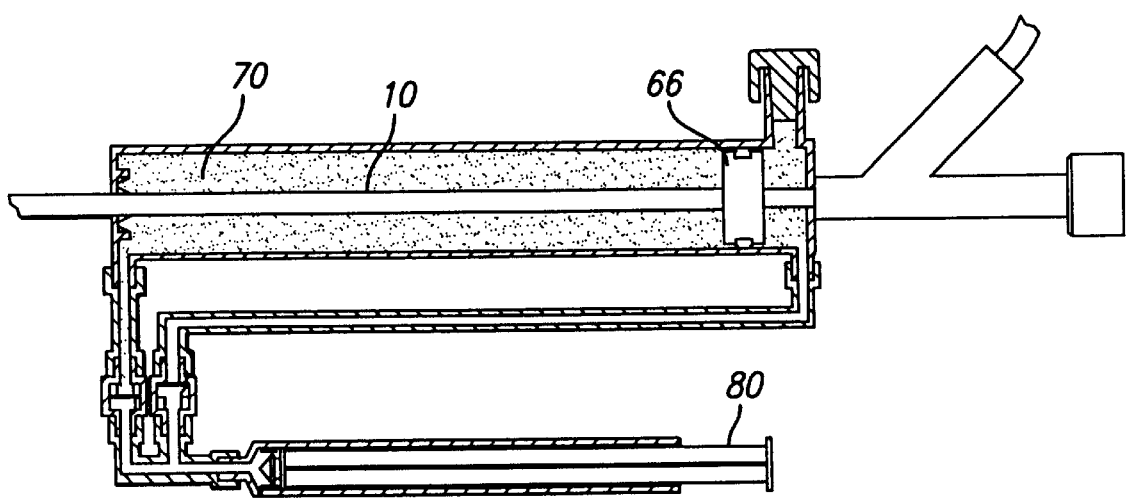

Referring to FIG. 11, the plunger 80 is pressed inward to open the valve 78 and move fluid through the conduit 74 into the piston chamber 70, thus moving the piston 66 to the right by a fixed amount and, in turn, retracting the outer sheath 10 from the stent. In the present embodiment, one stroke of the plunger 80 provides approximately 1 cm of travel of the piston 66. The plunger and piston are sized to provide a mechanical advantage of approximately 4:1. By repeatedly operating the plunger, the piston 66 will be drawn back to its fully deployed position as illustrated in FIG. 12. At this point, the outer sheath 10 is fully withdrawn from the stent 16, and the catheter 11 can be pulled out of the patient as described above.

Although the described embodiment employs a plunger which is manually operated, a lever or trigger mechanism could be employed to actuate the plunger 80. Such mechanism would include a spring return or the like to bias the plunger to the extended position. The use of a lever mechanism (in which case the plunger orientation would be reversed and a lever handle coupled to it) would allow grip pressure to be utilized as opposed to finger or thumb pressure.

Referring to FIGS. 13–16, a third embodiment of the invention will be described. This embodiment employs a rack and pinion mechanism actuated by means of a thumb knob. In FIG. 13, the device includes a housing 82 within which is carried a rack 84, movable from left to right as illustrated in FIGS. 15 and 16. The rack 84 interacts with a rack drive gear 86 coupled to a reduction drive gear 88, which in turn is driven by a knob 90 having a gear 92. The outer sheath 10 is coupled to the rack 84 to be movable therewith. FIG. 14 is a cross-sectional view of FIG. 13 along line 14—14, showing a different perspective of knob 90 in relation to housing 82.

In operation, the knob 90 is rotated counterclockwise as illustrated in FIG. 15, causing the gear 92 to move in the same direction. This action causes the reduction drive gear 88 and the rack drive gear 86 to move in a clockwise position, which in turn causes the rack 84 to retract within the housing by a distance of approximately 1 cm per revolution of the knob as indicated at 94. The mechanical advantage is controlled by appropriate sizing of the gears which drive the rack 84. After a sufficient number of rotations, the rack 84 will be fully retracted, as illustrated in FIG. 16 and the outer sheath 10 will be completely removed from the stent 16 so that the catheter 11 can be removed from the patient as described above.

Referring to FIGS. 17–20, a fourth embodiment of the delivery system will be described. In this embodiment, a power screw drive system is employed. A drive knob 96 is carried within a collar 98 of a housing 100. The drive knob 96 is fixed to a power nut 102 having a threaded interior surface which mates with the threaded surface of a power screw 104 which is slidably carried within the housing 100. The outer sheath 10 is coupled to the power screw 104 to move in conjunction therewith. By rotating the drive knob 96, the power nut 102 rotates and drives the power screw 104 to the right as shown in the FIGS. 19 and 20. FIG. 18 is an end plan view, illustrating the drive knob 96 within the collar 98. The mechanical advantage of this fourth embodiment is determined by the pitch of the power screw 104 and the size of the knob 96.

As shown in FIG. 19, a single rotation of the knob 96 achieves a movement of the power screw 104 of approximately 1 cm, as indicated at 106. The high mechanical advantage provided by the configuration facilitates smooth retraction of the outer sheath 10. After a number of rotations of the knob 96, the power screw 104 will be fully retracted, as illustrated in FIG. 20, and the outer sheath 10 will be completely withdrawn from the stent 16. The catheter 11 can then be removed as described above.

In summary, each of the disclosed systems provides a significant mechanical advantage which facilitates smooth retraction of the outer sheath 10 which covers the stent 16. This minimizes migration of the stent 10 during sheath retraction, thus ensuring that the stent 16 will remain in its desired location. In addition, various configurations are provided which are operable in numerous orientations, thus providing convenient and simple use during surgery.

Many alterations and modifications may be made by those having ordinary skill in the art without departing from the spirit and scope of the present invention. For example, a shape memory metal stent has been illustrated as being the type of stent that is to be delivered by the delivery mechanism of the present invention. It should be apparent, however, that the inventive concepts described above would be equally applicable to other types of expandable stents. Moreover, the words used in this specification to describe the invention and its various embodiments are to be understood not only in the sense of their commonly defined meanings, but to include by special definition in this specification structure, material or acts beyond the scope of the commonly defined meanings. Thus, if an element can be understood in the context of this specification as including more than one meaning, then its use in a claim must be understood as being generic to all possible meanings supported by the specification and by the word itself. The definitions of the words or elements of the following claims are, therefore, defined in this specification to include not only the combination of elements which are literally set forth, but all equivalent structure, material or acts for performing substantially the same function in substantially the same way to obtain substantially the same result. The described embodiments are to be considered illustrative rather than restrictive. The invention is further defined by the following claims.

What is claimed is:

1. An apparatus for introducing a stent into a body vessel, comprising:
    an elongated housing, providing a passage therein, wherein said housing further comprises a stationary ratchet on a first side, a movable ratchet on a second side directly opposite said first side, and a pinion engaging said movable ratchet;
    a movable member disposed within said passage;
    actuating means coupled to said housing for incrementally moving said movable member in a first direction;
    a catheter coupled to said movable member;
    an inner tube extending through said catheter;
    a tip attached to said inner tube; and
    a stabilizing element extending through said catheter for maintaining the position of the stent during retraction of said catheter.

2. The apparatus according to claim 1, wherein said movable member comprises a pawl hub, including a first and second spring pawl, wherein said first spring pawl is located on a first side of said pawl hub engaging said stationary ratchet, and said second spring pawl is located on a second side directly opposite said first side of said pawl hub engaging said movable ratchet.

3. The apparatus according to claim 1, wherein said actuating means comprises a lever handle coupled to said housing including a drive gear engaging said pinion.

4. The apparatus according to claim 3, further comprising a spring disposed between said housing and said lever handle, biasing said lever handle in an open position.

5. The apparatus according to claim 1, further comprising a withdrawing element for proximally withdrawing said inner tube and a locking mechanism, wherein said withdrawing element is attached to said inner tube and said locking mechanism is releasably coupled to said withdrawing element.

6. An apparatus for introducing a stent into a body vessel, comprising:
    an elongated housing, providing a passage therein;
    a plunger chamber coupled to said housing;
    an inlet conduit providing a path for fluid from said plunger chamber to said housing, including a directional check valve;
    an outlet conduit providing a path for fluid from said housing to said plunger chamber, including a directional check valve; and
    a fluid port for inserting fluid into said housing;
    a movable member disposed within said passage;
    actuating means coupled to said housing for incrementally moving said movable member in a first direction;
    a catheter coupled to said movable member;
    an inner tube extending through said catheter;
    a tip attached to said inner tube; and
    a stabilizing element extending through said catheter for maintaining the position of the stent during retraction of said catheter.

7. The apparatus according to claim 6, wherein said movable member comprises a piston.

8. The apparatus according to claim 6, wherein said actuating means comprises a plunger disposed within said plunger chamber for moving fluids to and from said housing.

9. An apparatus for introducing a stent into a body vessel, comprising:
- an elongated housing, providing a passage therein;
- a movable member disposed within said passage;
- a rack drive gear coupled to a reduction drive gear, wherein said rack drive gear engages said movable member;
- actuating means coupled to said housing for incrementally moving said movable member in a first direction;
- a catheter coupled to said movable member;
- an inner tube extending through said catheter;
- a tip attached to said inner tube; and
- a stabilizing element extending through said catheter for maintaining the position of the stent during retraction of said catheter.

10. The apparatus according to claim 9, wherein said movable member comprises a rack element.

11. The apparatus according to claim 9, wherein said actuating means comprises a knob coupled to a knob gear, wherein said knob gear engages said reduction drive gear.

12. An apparatus for introducing a stent into a body vessel, comprising:
- an elongated housing, providing a passage therein;
- a movable member disposed within said passage, comprising a power screw that has a threaded exterior surface;
- actuating means coupled to said housing for incrementally moving said movable member in a first direction;
- a catheter coupled to said movable member;
- an inner tube extending through said catheter;
- a tip attached to said inner tube; said
- a stabilizing element extending through said catheter for maintaining the position of the stent during retraction of said catheter.

13. The apparatus according to claim 12, wherein said actuating means comprises a drive knob coupled to a power nut, wherein said power nut has a threaded interior surface that mates with the threaded exterior surface of said power screw.

14. An apparatus for introducing a stent into a body vessel, comprising:
- an elongated housing, providing a passage therein, wherein said housing further comprises a stationary ratchet on a first side, a movable ratchet on a second side directly opposite said first side, and a pinion engaging said movable ratchet;
- a pawl hub disposed within said passage, including a first and second spring pawl, wherein said first spring pawl is located on a first side of said pawl hub engaging said stationary ratchet, and said second spring pawl is located on a second side directly opposite said first side of said pawl hub engaging said movable ratchet;
- a lever handle coupled to said housing, including a drive gear engaging said pinion;
- a catheter coupled to said pawl hub,
- an inner tube extending through said catheter;
- a tip attached to said inner tube; and
- a stabilizing element extending through said catheter for maintaining the position of the stent during retraction of said catheter.

15. The apparatus according to claim 14, wherein said stabilizing element comprises a tube spring coupled to a holding member, wherein said holding member grips a proximal end of the stent.

16. The apparatus according to claim 15, wherein said holding member is cup-shaped.

17. The apparatus according to claim 14, further comprising a spring disposed between said housing and said lever handle, biasing said lever handle in an open position.

18. The apparatus according to claim 14, further comprising a withdrawing element for proximally withdrawing said inner tube and a locking mechanism, wherein said withdrawing element is attached to said inner tube and said locking mechanism is releasably coupled to said withdrawing element.

19. The apparatus according to claim 14, wherein said tip is radiopaque.

20. An apparatus for introducing a stent into a body vessel, comprising:
- an elongated housing, providing a passage therein including a port for inserting fluid;
- a piston disposed within said passage;
- a plunger chamber coupled to said housing;
- an inlet conduit providing a path for fluid from said plunger chamber to said housing, including a directional check valve;
- an outlet conduit providing a path for fluid from said housing to said plunger chamber, including a directional check valve;
- a plunger disposed within said plunger chamber for moving fluids to and from said housing;
- a catheter coupled to said piston,
- an inner tube extending through said catheter;
- a tip attached to said inner tube; and
- a stabilizing element extending through said catheter for maintaining the position of the stent during retraction of said catheter.

21. The apparatus according to claim 20, wherein said stabilizing element comprises a tube spring coupled to a holding member, wherein said holding member grips a proximal end of the stent.

22. The apparatus according to claim 21, wherein said holding member is cup-shaped.

23. The apparatus according to claim 20, wherein said tip is radiopaque.

24. An apparatus for introducing a stent into a body vessel, comprising:
- an elongated housing, providing a passage therein;
- a rack element disposed within said passage;
- a reduction drive gear coupled to said housing;
- a rack drive gear coupled to said reduction drive gear, wherein said rack drive gear engages said rack element;
- a knob including a knob gear, wherein said knob gear engages said reduction drive gear;
- a catheter coupled to said rack element,
- an inner tube extending through said catheter;
- a tip attached to said inner tube; and
- a stabilizing element extending through said catheter for maintaining the position of the stent during retraction of said catheter.

25. The apparatus according to claim 24, wherein said stabilizing element comprises a tube spring coupled to a holding member, wherein said holding member grips a proximal end of the stent.

26. The apparatus according to claim 25, wherein said holding member is cup-shaped.

27. The apparatus according to claim 24, wherein said tip is radiopaque.

28. An apparatus for introducing a stent into a body vessel, comprising:
- an elongated housing, providing a passage therein;
- a power screw disposed within said passage, including a threaded exterior surface;
- a drive knob coupled to said housing;
- a power nut coupled to said drive knob, wherein said power nut has a threaded interior surface that mates with the threaded exterior surface of said power screw;
- a catheter coupled to said power screw,
- an inner tube extending through said catheter;
- a tip attached to said inner tube; and
- a stabilizing element extending through said catheter for maintaining the position of the stent during retraction of said catheter.

29. The apparatus according to claim 28, wherein said stabilizing element comprises a tube spring coupled to a holding member, wherein said holding member grips a proximal end of the stent.

30. The apparatus according to claim 29, wherein said holding member is cup-shaped.

31. The apparatus according to claim 28, wherein said tip is radiopaque.

* * * * *